US00PP18357P2

(12) United States Plant Patent
Hooijman

(10) Patent No.: US PP18,357 P2
(45) Date of Patent: Dec. 25, 2007

(54) ***LIMONIUM* PLANT NAMED 'ESM QUETZAL'**

(50) Latin Name: *Limonium sinense*
Varietal Denomination: Esm Quetzal

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 11/489,200

(22) Filed: Jul. 19, 2006

(51) Int. Cl.
*A01H 5/00* (2006.01)

(52) U.S. Cl. ..... Plt./358
(58) Field of Classification Search ..... Plt./358
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Limonium* plant named 'Esm Quetzal', characterized by its erect, long and strong flowering stems; vigorous growth habit; freely flowering habit; small light orange-colored flowers with red-colored venation; and good postproduction longevity.

1 Drawing Sheet

Botanical designation: *Limonium sinense.*
Cultivar denomination: 'Esm Quetzal'.

CROSS-REFERENCED TO RELATED APPLICATION

*Limonium* Plant Named 'Esm Amazona'; applicant, Aloysius A. J. Hooijman; filed concurrently.

BACKGROUND OF THE INVENTION

The present invention relates to a new and distinct cultivar of *Limonium* plant, botanically known as *Limonium sinense,* grown commercially as a cut flower, and hereinafter referred to by the name 'Esm Quetzal'.

The new *Limonium* is a product of a planned breeding program conducted by the Inventor in El Quinche, Pichincha, Ecuador. The objective of the breeding program is to create new freely flowering *Limonium* cultivars with long and straight flowering stems.

The new *Limonium* originated from a open-pollination in El Quinche, Pichincha, Ecuador in August, 2000 of a proprietary selection of *Limonium sinense* identified as Line 52, not patented, as the female, or seed, parent with an unknown selection of *Limonium sinense.* The cultivar 'Esm Quetzal' was discovered and selected by the Inventor as a flowering plant from within the progeny of the stated open-pollination in a controlled environment in El Quinche, Pichincha, Ecuador.

Asexual reproduction of the new *Limonium* by cuttings in a controlled environment in El Quinche, Pichincha, Ecuador since August, 2001, has shown that the unique features of this new *Limonium* are stable and reproduced true to type in successive generations.

SUMMARY OF THE INVENTION

The cultivar 'Esm Quetzal' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Esm Quetzal'. These characteristics in combination distinguish 'Esm Quetzal' as a new and distinct cultivar of *Limonium:*

1. Erect, long and strong flowering stems.
2. Vigorous growth habit.
3. Freely flowering habit.
4. Small light orange-colored flowers with red-colored venation.
5. Good postproduction longevity.

In side-by-side comparisons conducted in El Quinche, Pichincha, Ecuador, plants of the new *Limonium* differed from plants of the female parent selection in the following characteristics:

1. Plants of the new *Limonium* were more vigorous than plants of the female parent selection.
2. Inflorescence structure of the new *Limonium* was not as open and loose as inflorescence structure of plants of the female parent selection.

Plants of the new *Limonium* can be compared to plants of the cultivar 'Esm Amazona', disclosed in a U.S. Plant patent application filed concurrently. Plants of the new *Limonium* and the cultivar Esm Amazona differ primarily in flower color.

Plants of the new *Limonium* can be compared to plants of the *Limonium* cultivar China Pink, not patented. In side-by-side comparisons conducted in El Quinche, Pichincha, Ecuador, plants of the new *Limonium* differed from plants of the cultivar China Pink in the following characteristics:

1. Plants of the new *Limonium* produced more flowering stems than plants of the cultivar China Pink.
2. Plants of the new *Limonium* had stronger flowering stems than plants of the cultivar China Pink.
3. Plants of the new *Limonium* had longer postproduction longevity than plants of the cultivar China Pink.
4. Plants of the new *Limonium* and the cultivar China Pink differed in flower color as plants of the cultivar China Pink had pink-colored flowers.

BRIEF DESCRIPTION OF THE PHOTOGRAPHS

The accompanying photographs illustrate the overall appearance of the new *Limonium.* These photographs show the colors as true as it is reasonably possible to obtain in colored reproductions of this type. Colors in the photographs may differ slightly from the color values cited in the detailed botanical description which accurately describe the colors of the new *Limonium*. Clockwise from the upper left photograph:

side perspective view of a typical flowering stem;

close-up view of a typical inflorescence;

close-up view of a typical flowering stem; and close-up view of upper and lower surfaces of typical leaves of 'Esm Quetzal'.

DETAILED BOTANICAL DESCRIPTION

In the following description, color references are made to The Royal Horticultural Society Colour Chart, 2001 Edition, except where general terms of ordinary dictionary significance are used. The following observations and measurements describe plants grown during the winter in El Quinche, Pichincha, Ecuador in ground beds in a polyethylene-covered greenhouse and under conditions and practices which approximate those generally used in commercial cut *Limonium* production. During the production of the plants, day temperatures ranged from 11° C. to 28° C., night temperatures ranged from 5° C. to 11° C. and light levels ranged from 1,000 to 1,150 foot-candles. Plants were pinched. Measurements and numerical values represent averages for typical five-month old flowering plants.

Botanical classification: *Limonium sinense* cultivar 'Esm Quetzal'.

Commercial classification: Cut flower *Limonium*.

Parentage:

*Female, or seed, parent.*—Proprietary selection of *Limonium sinense* identified as Line 52, not patented.

*Male, or pollen, parent.*—Unknown selection of *Limonium sinense,* not patented.

Propagation:

*Type.*—By cuttings.

*Time to initiate roots.*—About 15 to 20 days at 17° C. to 25° C.

*Time to produce a rooted cutting.*—About seven to nine weeks at 17° C. to 25° C.

*Root description.*—Thick; 161C in color.

Plant description:

*Appearance.*—Perennial subshrub grown as a cut flower. Erect and strong flowering stems; inverted triangle form. Leaves basal. Freely flowering habit; numerous flowers arranged in symmetrical and moderately dense compound panicles. Vigorous growth habit.

*Branching habit.*—After pinching, about 38 flowering stems develop per year.

*Plant height.*—About 113 cm.

*Plant diameter or spread.*—About 82 cm.

*Flowering stems.*—Length: About 113 cm. Diameter: About 5 mm. Internode length: About 3.8 cm. Strength: Strong. Texture: Immature, pubescent; mature, glabrescent. Color: 137B.

Foliage description:

*Arrangement.*—Alternate, simple; sessile.

*Length.*—About 28.1 cm.

*Width.*—About 4.4 cm.

*Shape.*—Narrowly obovate.

*Apex.*—Acute.

*Base.*—Attenuate.

*Margin.*—Crenate; undulate.

*Texture, upper and lower surfaces.*—Smooth, glabrous; waxy.

*Venation pattern.*—Pinnate.

*Color.*—Developing foliage, upper surface: 137B. Developing foliage, lower surface: 146B to 138B. Fully expanded foliage, upper surface: 137A; venation, 147C. Fully expanded foliage, lower surface: 138B; venation, 145C.

Flower description:

*Flower arrangement and habit.*—Compound cymes with numerous flowers; flowers actinomorphic and symmetrical. Very freely flowering, about 2,300 flowers per inflorescence. Flowers face mostly upright.

*Flowering response.*—In Ecuador, plants flower year round. Plants begin flowering about 15 weeks after planting.

*Post-production longevity.*—As a cut flower, flowers last for about two weeks. Corolla self-cleaning; calyx persistent.

*Fragrance.*—None detected.

*Inflorescence height.*—About 113 cm.

*Inflorescence diameter.*—About 40 cm.

*Flower diameter.*—About 5 mm.

*Flower depth (height).*—About 9 mm.

*Flower buds.*—Length: About 6 mm. Diameter: About 1 mm. Shape: Fusiform. Color: Apex and mid-section: 184C to N199A. Base: 144C.

*Corolla.*—Petals per flower: Five. Petal length: About 8 mm. Petal width: About 2 mm. Petal shape: Triangular. Petal apex: Emarginate. Petal margin: Entire. Petal texture, upper and lower surfaces: Smooth, glabrous; membraneous. Petal color: When opening, upper surface: 6A; towards the base, close to 155D. When opening, lower surface: 3B; towards the base, close to 155D. Fully opened, upper surface: 3A; towards the base, close to 155D. Fully opened, lower surface: 2A; towards the base, close to 155D.

*Calyx.*—Sepals per flower: Five. Length: About 7 mm. Width: About 7 mm. Shape: Salverform. Sepal apex: Acute. Sepal margin: Entire. Sepal texture, upper and lower surfaces: Smooth, glabrous. Sepal color: When opening, upper and lower surfaces: 27D; veins, N34C; throat, 144D. Fully opened, upper and lower surfaces: 27B; veins, N34C; throat, 144D.

*Pedicels.*—Length: About 14.7 cm. Diameter: About 5 mm. Strength: Strong. Angle: About 32° from vertical. Texture: Smooth, glabrous. Color: 137B.

*Reproductive organs.*—Stamens: Quantity per flower: Five. Anther shape: Reniform. Anther length: Less than 1 mm. Anther color: 151C. Pollen amount: Abundant. Pollen color: 151C. Pistils: Quantity per flower: One. Pistil length: About 6 mm. Style length: About 4 mm. Style color: Close to 155D. Stigma shape: Filiform. Stigma color: 154B. Ovary color: 154D. Seeds: Seed development has not been observed.

Disease/pest resistance: Plants of the new *Limonium* have been observed to be resistant to *Peronospora*. Plants have not been shown to be resistant to pests and other pathogens common to *Limonium*.

Temperature tolerance: Plants of the new *Limonium* have been observed to tolerate temperatures ranging from about 5° C. to about 30° C.

It is claimed:

1. A new and distinct *Limonium* plant named 'Esm Quetzal' as illustrated and described.

* * * * *

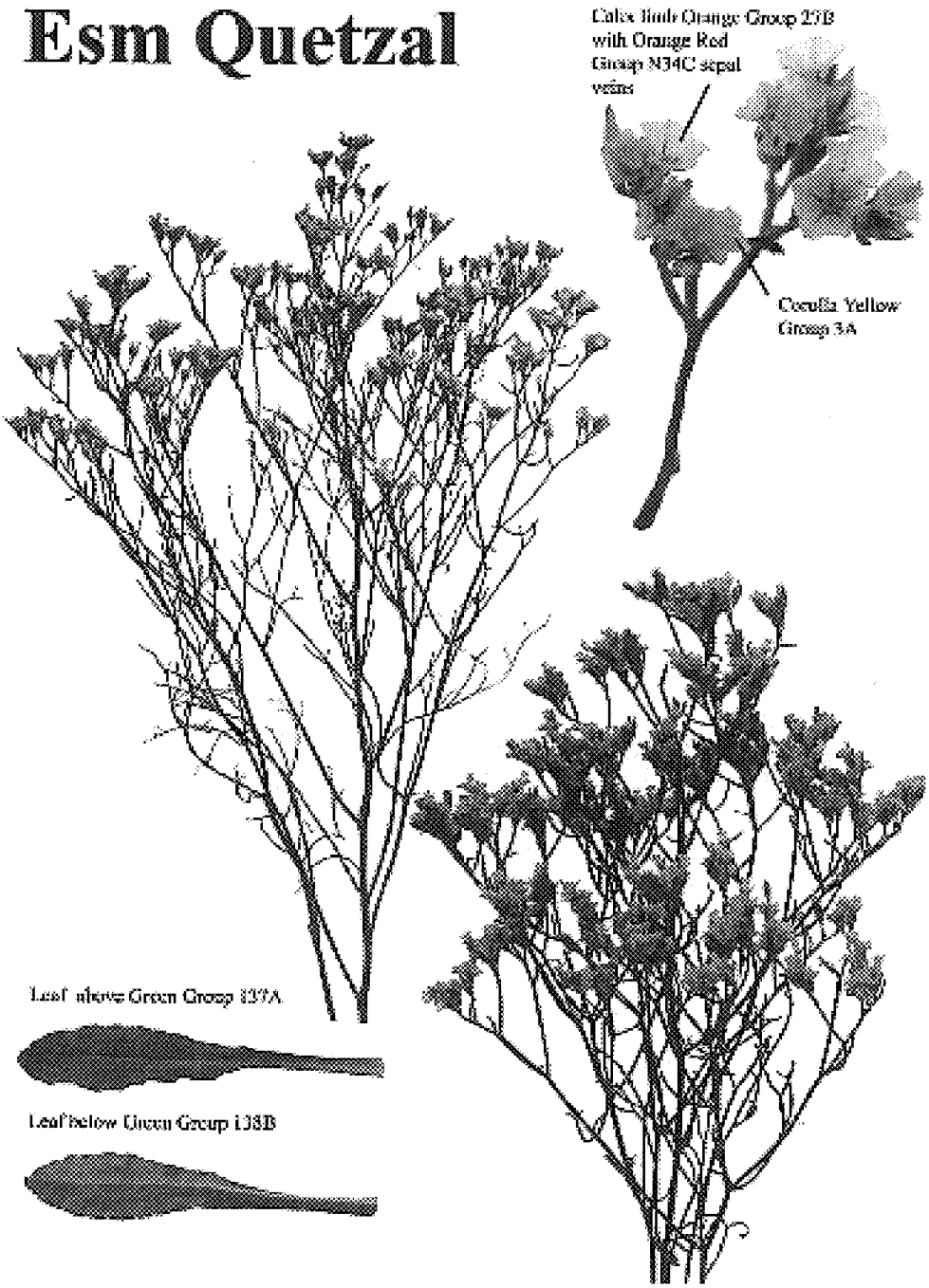
Esm Quetzal
Calyx Bud Orange Group 27B with Orange Red Group N34C sepal veins
Corolla Yellow Group 3A
Leaf above Green Group 137A
Leaf below Green Group 138B